US012569488B2

(12) United States Patent
Chen et al.

(10) Patent No.: US 12,569,488 B2
(45) Date of Patent: Mar. 10, 2026

(54) METHODS FOR PREDICTING RESPONSE TO ARGININE DEPRIVATION THERAPY BASED ON PLASMA ARGININE LEVELS IN CANCER PATIENTS

(71) Applicant: Polaris Pharmaceuticals. Inc., San Diego, CA (US)

(72) Inventors: Hung-Wen Chen, Taipei City (TW); Shaw Tsen Chen, Taipei City (TW); Hui-Fen Liu, Taipei City (TW); Chih-Ling Kuo, Taipei City (TW); Chiung-Fang Shiu, Taipei City (TW)

(73) Assignee: POLARIS PHARMACEUTICALS, INC., San Diego, CA (US)

( * ) Notice: Subject to any disclaimer, the term of this patent is extended or adjusted under 35 U.S.C. 154(b) by 283 days.

(21) Appl. No.: 18/178,259

(22) Filed: Mar. 3, 2023

(65) Prior Publication Data

US 2024/0293407 A1      Sep. 5, 2024

(51) Int. Cl.
| | |
|---|---|
| *A61K 31/337* | (2006.01) |
| *A61K 31/513* | (2006.01) |
| *A61K 31/519* | (2006.01) |
| *A61K 31/555* | (2006.01) |
| *A61K 33/243* | (2019.01) |
| *A61K 38/50* | (2006.01) |
| *A61K 39/395* | (2006.01) |
| *A61K 45/06* | (2006.01) |
| *A61P 35/00* | (2006.01) |
| *C07K 16/28* | (2006.01) |
| *C12N 9/78* | (2006.01) |

(52) U.S. Cl.
CPC .......... *A61K 31/519* (2013.01); *A61K 31/513* (2013.01); *A61K 31/555* (2013.01); *A61K 33/243* (2019.01); *C07K 16/2818* (2013.01); *C12N 9/78* (2013.01); *C12Y 305/03006* (2013.01)

(58) Field of Classification Search
CPC .. A61K 31/519; A61K 31/513; A61K 31/555; A61K 33/243; C07K 16/2818; C12N 9/78; C12Y 305/03006
See application file for complete search history.

(56) References Cited

FOREIGN PATENT DOCUMENTS

WO      WO-2015051340 A1 *   4/2015   .............. A61P 31/04

OTHER PUBLICATIONS

Cao, Y. et al. BMC Cancer, 2016, 16, 343 (Year: 2016).*
Szlosarek, P. W. et al. Cancer Medicine, 2021, 10, 6642-6652 (Year: 2021).*

* cited by examiner

*Primary Examiner* — Clinton A Brooks
*Assistant Examiner* — Kendall Nicole Heitmeier
(74) *Attorney, Agent, or Firm* — Muncy, Geissler, Olds & Lowe, P.C.

(57) ABSTRACT
A method for providing a prediction as to whether a subject with a cancer exhibits a beneficial response to arginine deprivation therapy including determining the plasma level of arginine in the subject, followed by administering to the subject an arginine deprivation therapy alone or in combination with an anti-cancer agent based on the determined plasma level of arginine. According to some embodiments of the present disclosure, the anti-cancer agent is selected from the group consisting of FOLFOX, docetaxel, cisplatin, pemetrexed, pembrolizumab, and a combination thereof.

13 Claims, 12 Drawing Sheets

METHODS FOR PREDICTING RESPONSE TO ARGININE DEPRIVATION THERAPY BASED ON PLASMA ARGININE LEVELS IN CANCER PATIENTS

BACKGROUND OF THE INVENTION

1. Field of the Invention

The present disclosure in general relates to the field of cancer treatment. More particularly, the present disclosure relates to methods of treating cancers via arginine deprivation therapy.

2. Description of Related Art

Cancer is a group of diseases characterized by the development of abnormal cells that divide uncontrollably and exhibit the ability to infiltrate and destroy normal tissues. Cancer is the second-leading cause of death in the world that accounts for nearly 10 million death every year, in which the most common causes of cancer death include, lung cancer, colorectal cancer, liver cancer, gastric cancer and breast cancer. The treatment of cancer varies with the type and stage of the cancer. The mainstays of cancer treatment include surgery, chemotherapy, radiotherapy, immunotherapy, hormone therapy and targeted therapy. However, none of the treatments produce a satisfactory effect, and a variety of adverse responses are observed in cancer patients. Accordingly, there is a continuing interest in the identification and development of alternative approaches for treating cancers.

Certain cancers are auxotrophic for a particular amino acid (e.g., arginine), and amino acid deprivation (e.g., arginine deprivation) may provide a potential means to treat these cancers. Arginine can be degraded by several enzymes, including arginine deiminase (ADI), a microbial enzyme from mycoplasma that exhibits high affinity to arginine and catalyzes arginine to citrulline and ammonia. Citrulline can be recycled back to arginine in normal cells which express argininosuccinate synthetase 1 (ASS1). A pegylated form of ADI (ADI-PEG 20) has been formulated and shown in clinical trials for targeting arginine auxotrophic tumors by arginine deprivation therapy. Resistance to ADI is often developed through the reactivation or upregulation of ASS1. Further, it is reported that prolonged treatment with ADI may lead to the activation of different cellular pathways associated with resistance to apoptosis, possibly limiting the overall treatment window for ADI.

Accordingly, there exist in the related art a need of therapeutic strategies to optimize the arginine deprivation therapy thereby improving the treatment outcomes in cancer patients.

SUMMARY OF THE INVENTION

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based on, at least in part, the discovery that the plasma level of arginine is associated with cancer patients' response to a pegylated form of ADI (ADI- PEG 20) based therapy. Therefore, the plasma level of arginine can be used to predict the therapeutic response of a cancer patient to arginine deprivation therapy, and used as a guide for tailoring suitable therapy regime individually.

Accordingly, the present disclosure is directed to a method of treating a cancer in a subject. The method comprises, (a) determining the plasma level of arginine in the subject; and (b) administering to the subject an arginine deprivation therapy alone or in combination with an anti-cancer agent based on the determined plasma level of arginine in step (a).

According to the embodiments of the present disclosure, the arginine deprivation therapy comprises administering to the subject an agent selected from the group consisting of difluoromethylornithine (DFMO), a recombinant arginine deiminase (rADI), a recombinant arginase (rArg), a recombinant arginine decarboxylase (rADC), a pegylated form of rADI (hereinafter as "pegylated rADI"), a pegylated form of rArg (hereinafter as "pegylated rArg"), a pegylated form of rADC (hereinafter as "pegylated rADC"), and a combination thereof. According to some embodiments of the present disclosure, the anti-cancer agent is selected from the group consisting of FOLFOX, docetaxel, cisplatin, pemetrexed, pembrolizumab, and a combination thereof.

According to some embodiments, the pegylated rADI and FOLFOX are independently administered to the subject when the plasma level of arginine in step (a) is equal to or greater than 34 micromole per liter ($\geq$34 $\mu$mol/L). In some exemplary embodiments, the pegylated rADI is administered in an amount of about 36 mg/m$^2$ body surface area weekly, and FOLFOX is administered biweekly.

According to some embodiments, the pegylated rADI and pembrolizumab are independently administered to the subject when the plasma level of arginine in step (a) is equal to or greater than 60.2 $\mu$mol/L ($\geq$60.2 $\mu$mol/L). In some exemplary embodiments, the pegylated rADI is administered in an amount of about 36 mg/m$^2$ body surface area weekly, and pembrolizumab is administered in the amount of about 200 mg every three weeks.

According to certain embodiments, the pegylated rADI, pemetrexed and cisplatin are independently administered to the subject when the plasma level of arginine in step (a) is equal to or greater than 68.2 $\mu$mol/L ($\geq$68.2 $\mu$mol/L). In certain exemplary embodiments, the pegylated rADI is administered in an amount of about 36 mg/m$^2$ body surface area weekly, pemetrexed is administered in an amount of about 500 mg/m$^2$ body surface area every three weeks, and cisplatin is administered in an amount of about 75 mg/m$^2$ body surface area every three weeks.

According to certain embodiments, the pegylated rADI is administered to the subject alone when the plasma level of arginine in step (a) is equal to or greater than 84.2 $\mu$mol/L ($\geq$84.2 $\mu$mol/L). In some preferred embodiments, the pegylated rADI is administered in an amount of about 18 mg/m$^2$ body surface area weekly.

According to some embodiments, the pegylated rADI and docetaxel are independently administered to the subject when the plasma level of arginine in step (a) is equal to or greater than 97.5 $\mu$mol/L ($\geq$97.5 $\mu$mol/L). In certain exemplary embodiments, the pegylated rADI is administered in an amount of about 36 mg/m$^2$ body surface area weekly, and docetaxel is administered in an amount of about 75 mg/m$^2$ body surface area every three weeks.

According to some embodiments, the pegylated rADI and cisplatin are independently administered to the subject when the plasma level of arginine in step (a) is equal to or greater than 122 µmol/L (≥122 µmol/L). In some exemplary embodiments, the pegylated rADI is administered in an amount of about 36 mg/m$^2$ body surface area weekly, and cisplatin is administered in an amount of about 30 mg/m$^2$ body surface area weekly for three weeks followed by one week of rest.

Examples of cancer treatable with the present method (i.e., arginine deprivation therapy alone or in combination with an anti-cancer agent) include, but are not limited to, breast cancer, brain tumor, colorectal cancer, head and neck squamous cell carcinoma, hepatocellular carcinoma (HCC), leukemia (e.g., acute myeloid leukemia (AML)), lymphoma, lung cancer, melanoma, mesothelioma (e.g., malignant pleural mesothelioma (MPM)), neuroblastoma, ovarian cancer, pancreatic cancer, prostate cancer, renal cell carcinoma, and sarcoma.

The subject treatable with the present method is a mammal; preferably, a human.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE PREFERRED EMBODIMENTS

Figure 1:
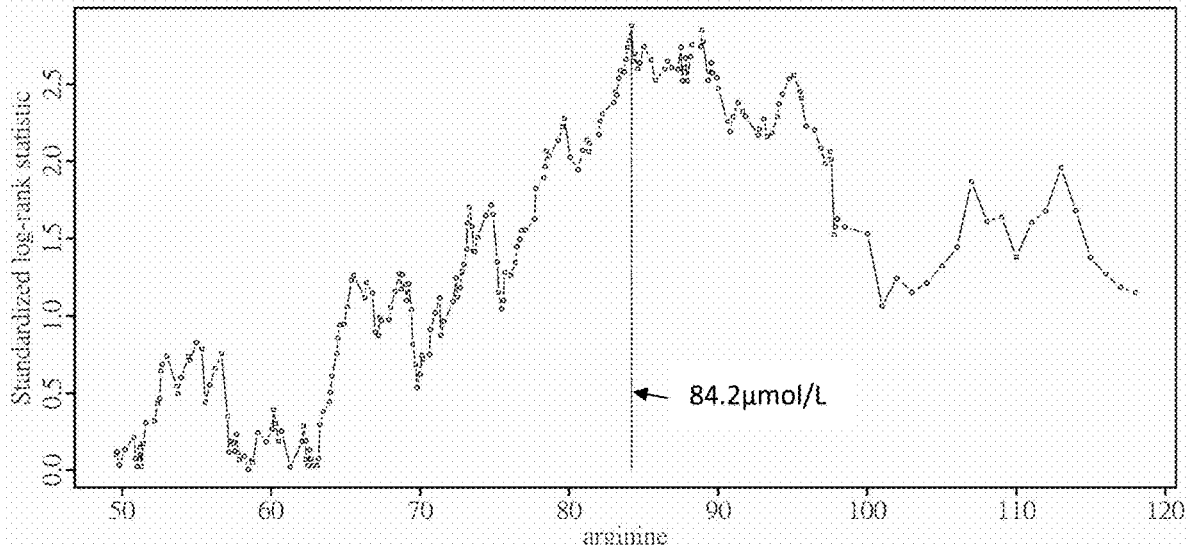
FIG. 1 shows the chart illustrating the treatment of cancer patients with ADI-PEG 20, analyzed via using the maximum log-rank statistic to finding the arginine cut-off.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. DEFINITIONS

As used herein, the term "hepatocellular carcinoma" (or "HCC" for short) refers to a malignant tumor of hepatocellular origin. HCC is a type of liver cancer. HCC may undergo hemorrhage and necrosis because of a lack of fibrous stroma. According to the Barcelona Clinic Liver Cancer (BCLC) staging system updated in 2022, HCC can be classified into five stages, including (1) stage 0 (very early stage), which is defined as the presence of a single nodule being equal to or less than 2 cm without vascular invasion or extrahepatic spread; (2) stage A (early stage), which is defined as the presence of one nodule irrespective of size or as a multifocal HCC up to 3 nodules, without vascular invasion or extrahepatic spread; (3) stage B (intermediate stage), which is defined as the presence of multifocal HCC without vascular invasion or extrahepatic spread; (4) stage C (advanced stage), which is defined as patients having portal invention and/or extrahepatic spread; and (5) stage D (end stage or terminal stage), which is defined as patients having major cancer-related symptoms and/or impaired liver function. Based on the classification of the BCLC system, the term "advanced hepatocellular carcinoma" or "advanced HCC" refers to a locally advanced HCC or a metastatic HCC (i.e., HCC that has spread from liver to another part of the body). In general, advanced HCC is unresectable (i.e., it has spread to surrounding tissue and cannot be surgically removed), and is not amenable to cure by local modalities of treatment, such as radiotherapy.

The term "arginine deprivation therapy" refers to compounds or agents that remove the supply of arginine to cancers with disrupted urea cycle, thereby halting the growth of the cancers and induce cell death.

The term "FOLFOX" refers to a chemotherapy made up of 5-fluorouracil (5-FU), folinic acid (leucovorin) and oxaliplatin. The term "FOLFOX" as used herein is not intended to be limited to any particular amounts of or dosing regimens for those components. Rather, as used herein, "FOLFOX" includes all combinations of those components in any amounts and dosing regimens. Based on the does and ways in which the three drugs are given, there are several different FOLFOX regimens known in the art, including FOLFOX-4, FOLFOX-6, modified FOLFOX-6 (mFOLFOX-6), and FOLFOX-7. According to some embodiments of the present disclosure, the FOLFOX is mFOLFOX-6.

As used herein, the term "survival", refers to the act or fact of living. The phrase "overall survival" (OS) refers to a prolongation in life expectancy as compared to naive or untreated individuals or patients.

The term "confidence interval" (CI) as used herein has its plain meaning known to one of ordinary skill in the art, and refers to a statistical range with a specified probability that a given parameter lies within the range.

The terms "administered" and "administering" are used interchangeably herein to refer a mode of delivery, including, without limitation, intravenously, intratumorally, intramuscularly, intraperitoneally, intraarterially, or subcutaneously administering a treatment (e.g., arginine deprivation therapy or anti-cancer agent).

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

The terms "cancer" and "tumor" are used alternatively in the present disclosure, and preferably refer to or describe the physiological condition in mammals that is typically characterized by unregulated cell growth. Cancers in this respect include metastases cancers, and/or drug-resistant cancers. Examples of cancer include, but are not limited to, breast cancer, brain tumor, colorectal cancer, head and neck squamous cell carcinoma, hepatocellular carcinoma (HCC), leukemia, acute myeloid leukemia (AML), lymphoma, lung cancer, melanoma, mesothelioma, malignant pleural mesothelioma (MPM), neuroblastoma, ovarian cancer, pancreatic cancer, prostate cancer, renal cell carcinoma, sarcoma, and a combination thereof.

Unless otherwise indicated, the terms "patient" and "subject" are used interchangeably in the present disclosure, and refer to an animal including the human species that is treatable by the method of the present invention. The term "patient" or "subject" is intended to refer to both the male and female gender unless one gender is specifically indicated.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

II. DESCRIPTION OF THE INVENTION (1) Prediction of Cancer Patients' Responses to Arginine Deprivation Therapy Diversity of cancer treatment responses has long been recognized, largely owing to the underlying heterogeneities in cancer biology, variations in physiological function and distinctions in patients genetic profiles. Therefore, one objective of the present disclosure aims at providing a molecular marker associated with the responses of cancer patients to arginine deprivation therapy. According to the embodiments of the present disclosure, the plasma level of arginine is associated with the therapeutic response of tumors (e.g., HCC) in patients to a pegylated form of ADI (ADI-PEG 20, an arginine deiminase conjugated to polyethylene glycol with 20,000 molecular weight) based therapy.

Accordingly, the first aspect of the present disclosure provides a method of making a prognosis as to whether a subject with a cancer (e.g., HCC) exhibits a beneficial response to arginine deprivation therapy. The method comprises, (a) determining the plasma level of arginine in the subject; and (b) making the prognosis based on the determined plasma level of arginine in step (a), wherein the plasma level of arginine being equal to or greater than 84.2 indicates that the subject exhibits a beneficial response to arginine deprivation therapy.

In step (a), the plasma level of arginine is measured. Suitable assays used to determine the plasma level of arginine include, but are not limited to, spectrophotometric method, capillary electrophoresis (CE), enzyme-linked immunosorbent assay (ELISA), high performance liquid chromatography (HPLC), mass spectrometry (MS), Sakaguchi test, biosensors, and a combination thereof.

Then, in step (b), a skilled artisan or a clinical practitioner may make the prognosis based on the plasma level of arginine. According to some embodiments of the present disclosure, the plasma level of arginine being equal to or greater than 84.2 μmol/L (≥84.2 μmol/L; e.g., 84.2, 84.3, 84.4, 84.5, 84.6, 84.7, 84.8, 84.9, 85, 85.1, 85.2, 85.3, 85.4, 85.5, 85.6, 85.7, 85.8, 85.9, 86, 86.1, 86.2, 86.3, 86.4, 86.5, 86.6, 86.7, 86.8, 86.9, 87, 87.1, 87.2, 87.3, 87.4, 87.5, 87.6, 87.7, 87.8, 87.9, 88, 88.1, 88.2, 88.3, 88.4, 88.5, 88.6, 88.7, 88.8, 88.9, 89, 89.1, 89.2, 89.3, 89.4, 89.5, 89.6, 89.7, 89.8, 89.9, 90, 90.1, 90.2, 90.3, 90.4, 90.5, 90.6, 90.7, 90.8, 90.9, 91, 91.1, 91.2, 91.3, 91.4, 91.5, 91.6, 91.7, 91.8, 91.9, 92, 92.1, 92.2, 92.3, 92.4, 92.5, 92.6, 92.7, 92.8, 92.9, 93, 93.1, 93.2, 93.3, 93.4, 93.5, 93.6, 93.7, 93.8, 93.9, 94, 94.1, 94.2, 94.3, 94.4, 94.5, 94.6, 94.7, 94.8, 94.9, 95, 95.1, 95.2, 95.3, 95.4, 95.5, 95.6, 95.7, 95.8, 95.9, 96, 96.1, 96.2, 96.3, 96.4, 96.5, 96.6, 96.7, 96.8, 96.9, 97, 97.1, 97.2, 97.3, 97.4, 97.5, 97.6, 97.7, 97.8, 97.9, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8, 99.9 or 100 μmol/L, or higher) indicates that the subject exhibits a beneficial response to arginine deprivation therapy. i.e., responding to arginine deprivation therapy in a positive manner. According to certain working examples, the beneficial response is associated with overall survival, in which compared to the subject with plasma level of arginine ≥84.2 μmol/L, the subject with plasma level of arginine ≥84.2 μmol/L has a longer overall survival post-treatment.

According to some embodiments of the present disclosure, the arginine deprivation therapy comprises administering to the subject (e.g., HCC patient) an agent selected from the group consisting of DFMO, rADI, rArg, rADC, pegylated rADI, pegylated rArg, pegylated rADC, and a combination thereof. In some exemplary embodiments, the pegylated rADI (ADI-PEG 20) is administered in an amount of about 18 mg/m² body surface area weekly, in which the median overall survival of the subjects with plasma level of arginine ≥84.2 μmol/L is about 8.6 months (with a 95% confidence interval (CI) ranging from 7.3 months to 10.5 months), and the median overall survival of the subjects with plasma level of arginine ≥84.2 μmol/L is about 5.7 months (with a 95% CI ranging from 4.9 months to 7.2 months) post-treatment.

Examples of the cancer include, but are not limited to, breast cancer, brain tumor, colorectal cancer, head and neck squamous cell carcinoma, HCC, leukemia, AML, lymphoma, lung cancer, melanoma, mesothelioma, MPM, neuroblastoma, ovarian cancer, pancreatic cancer, prostate cancer, renal cell carcinoma, sarcoma, and a combination thereof.

In some embodiments of the present disclosure, the cancer is HCC. According to one specific example, the cancer is advanced HCC.

(2) Prediction of Cancer Patients' Responses to Combined Treatment

According to some embodiments of the present disclosure, the arginine deprivation therapy is combined with one or more additional treatments so as to improve its therapeutic effect. Accordingly, the second aspect of the present disclosure pertains to a method of making a prognosis as to whether a subject with a cancer (e.g., HCC) exhibits a beneficial response to the combined treatment (i.e., arginine deprivation therapy plus additional treatment(s)). The method comprises the steps of, (a) determining the plasma level of arginine in the subject; and (b) making the prognosis based on the determined plasma level of arginine in step (a).

According to some embodiments of the present disclosure, the arginine deprivation agent is combined with FOLFOX treatment. In these embodiments, the plasma level of arginine being equal to or greater than 34 μmol/L (≥34 μmol/L; e.g., 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 μmol/L, or higher) indicates that the subject exhibits a beneficial response to the combined treatment, i.e., responding to the arginine deprivation therapy plus FOLFOX treatment in a positive manner. According to certain working examples, the beneficial response is associated with overall survival, in which compared to the subject with plasma level of arginine <34 μmol/L, the subject with plasma level of arginine ≥34 μmol/L has a longer overall survival post-treatment.

In some exemplary embodiments, the pegylated rADI (ADI-PEG 20) is administered in an amount of about 36 mg/m² body surface area weekly, and the FOLFOX treatment is administered biweekly, in which the median overall survival of the subjects with plasma level of arginine ≥34 μmol/L is about 9.5 months (with a 95% CI ranging from 7.5 months to 15.1 months), and the median overall survival of the subjects with plasma level of arginine ≤34 μmol/L is about 4.3 months (with a 95% CI ranging from 4.0 months to 4.6 months) post-treatment.

According to some embodiments of the present disclosure, the arginine deprivation therapy is combined with pembrolizumab. In these embodiments, the plasma level of arginine being equal to or greater than 60.2 μmol/L (≥60.2 μmol/L; e.g., 60.2, 60.3, 60.4, 60.5, 60.6, 60.7, 60.8, 60.9, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 μmol/L, or higher) indicates that the subject exhibits a beneficial response to the combined treatment, i.e., responding to the arginine deprivation therapy plus pembrolizumab treatment in a positive manner. According to certain working examples, the beneficial response is associated with overall survival, in which compared to the subject with plasma level of arginine <60.2 μmol/L, the subject with plasma level of arginine ≥60.2 μmol/L has a longer overall survival post-treatment.

In some exemplary embodiments, the pegylated rADI (ADI-PEG 20) is administered in an amount of about 36 mg/m² body surface area weekly, and pembrolizumab is administered in the amount of about 200 mg every three weeks.

According to certain embodiments of the present disclosure, the arginine deprivation agent is administered in combination with pemetrexed and cisplatin. In these embodiments, the plasma level of arginine being equal to or greater than 68.2 μmol/L (≥68.2 μmol/L; e.g., 68.2, 68.3, 68.4, 68.5, 68.6, 68.7, 68.8, 68.9, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 μmol/L, or higher) indicates that the subject exhibits a beneficial response to the combined treatment, i.e., responding to the arginine deprivation agent plus pemetrexed and cisplatin treatments in a positive manner. According to certain examples, the beneficial response is associated with overall survival, in which compared to the subject with plasma level of arginine <68.2 μmol/L, the subject with plasma level of arginine ≥68.2 μmol/L has a longer overall survival post-treatment.

In some exemplary embodiments, the pegylated rADI (ADI-PEG 20) is administered in an amount of about 36 mg/m² body surface area weekly, pemetrexed is administered in an amount of about 500 mg/m² body surface area every three weeks, and cisplatin is administered in an amount of about 75 mg/m² body surface area every three weeks. According to these embodiments, the median overall survival of the subjects with plasma level of arginine ≥68.2 μmol/L is about 12.5 months (with a 95% CI ranging from 9.8 months to 14.2 months), and the median overall survival of the subjects with plasma level of arginine <68.2 μmol/L is about 6.5 months (with a 95% CI ranging from 3.8 months to 8.8 months) post-treatment.

According to certain embodiments of the present disclosure, the arginine deprivation agent is administered in combination with docetaxel. In these embodiments, the plasma level of arginine being equal to or greater than 97.5 μmol/L (≥97.5 μmol/L; e.g., 97.5, 97.6, 97.7, 97.8, 97.9, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8, 99.9 or 100 μmol/L, or higher) indicates that the subject exhibits a beneficial response to the combined treatment, i.e., responding to the arginine deprivation therapy plus docetaxel treatment in a positive manner. According to certain working examples, the beneficial response is associated with overall survival, in which compared to the subject with plasma level of arginine <97.5 μmol/L, the subject with plasma level of arginine ≥97.5 μmol/L has a longer overall survival post-treatment.

In some exemplary embodiments, the pegylated rADI (ADI-PEG 20) is administered in an amount of about 36 mg/m² body surface area weekly, and docetaxel is administered in an amount of about 75 mg/m² body surface area every three weeks. According to these embodiments, the median overall survival of the subjects with plasma level of arginine ≥97.5 μmol/L is about 40.7 months (with a 95% CI ranging from 7.2 months to 40.7 months), and the median overall survival of the subjects with plasma level of arginine <97.5 μmol/L is about 14.6 months (with a 95% CI ranging from 5.7 months to 16.0 months) post-treatment.

According to some embodiments of the present disclosure, the arginine deprivation agent is administered in combination with cisplatin. In these embodiments, the plasma level of arginine being equal to or greater than 122 μmol/L (≥122 μmol/L; e.g., 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 μmol/L, or higher) indicates that the subject exhibits a beneficial response to the combined treatment, i.e., responding to the arginine deprivation agent plus cisplatin treatment in a positive manner. According to certain examples, the beneficial response is associated with overall survival, in which compared to the subject with plasma level of arginine <122 μmol/L, the subject with plasma level of arginine ≥122 μmol/L has a longer overall survival post-treatment.

In some exemplary embodiments, the pegylated rADI (ADI-PEG 20) is administered in an amount of about 36 mg/m² body surface area weekly, and cisplatin is administered in an amount of about 30 mg/m² body surface area weekly for three weeks (week 1 to week 3) followed by one week (week 4) of rest period in one treatment cycle. According to these embodiments, the median overall survival of the subjects with plasma level of arginine ≥122 μmol/L is about 15.7 months (with a 95% CI ranging from 8.9 months to 28.5 months), and the median overall survival of the subjects with plasma level of arginine <122 μmol/L is about 6.4 months (with a 95% CI ranging from 3.4 months to 8.2 months) post-treatment.

As described above, the cancer may be breast cancer, brain tumor, colorectal cancer, head and neck squamous cell carcinoma, HCC, leukemia, AML, lymphoma, lung cancer, melanoma, mesothelioma, MPM, neuroblastoma, ovarian cancer, pancreatic cancer, prostate cancer, renal cell carcinoma, sarcoma, or a combination thereof. According to some working examples, the cancer is HCC. In one specific example, the cancer is advanced HCC.

(3) Method of Treating Cancers

Another aspect of the present disclosure pertains to a method of treating cancers via arginine deprivation agent alone (i.e., the administration of DFMO, rADI, rArg, rADC, pegylated rADI, pegylated rArg, pegylated rADC, or a combination thereof) for arginine deprivation therapy, or in combination with one or more additional treatments. According to some embodiments of the present disclosure, the method comprises the steps of, (a) determining the plasma level of arginine in the subject; and (b) administering to the subject a suitable treatment based on the determined plasma level of arginine in step (a).

According to some embodiments of the present disclosure, in the case when the plasma level of arginine is equal to or greater than 34 μmol/L, then the pegylated rADI (ADI-PEG 20) and FOLFOX treatment are independently administered to the subject. In some exemplary embodiments, the pegylated rADI (ADI-PEG 20) is administered in an amount of about 36 mg/m² body surface area weekly, and the FOLFOX treatment is administered biweekly, so as to ameliorate or alleviate the symptoms associated with cancers. As could be appreciated, a skilled artisan or a clinical practitioner may adjust the treatment regimen (including the dosages, schedule and duration of ADI-PEG 20 and FOLFOX treatments) in accordance with practical requirements.

Alternatively, in the case when the plasma level of arginine is less than 34 μmol/L, then an alternative anti-cancer treatment is administered to the subject for therapeutic purpose, wherein the alternative anti-cancer treatment is preferably selected from the group consisting of surgery, chemotherapy, targeted therapy, radiotherapy, hormone therapy, immunotherapy, and a combination thereof. A skilled artisan or a clinical practitioner may choose a suitable treatment for the cancer patient in accordance with clinical factors such as age, sex and physical conditions of the patient, and the type and stage of the cancer.

The agents commonly used in chemotherapy include, but are not limited to, doxorubicin, adriamycin, bleomycin, actinomycin, dactinomycin, mutamycin, daunorubicin, epirubicin, idarubicin, mitoxantrone, mitomycin, epipodophyllotoxins, etoposide, teniposide, antimicrotubule agent, vinblastine, vincristine, vindesine, vinorelbine, taxane, paclitaxel (taxol), nitrogen mustard, chlorambucil, cyclophosphamide, estramustine, ifosfamide, mechlorethamine, melphalan, aziridines, thiotepa alkyl sulfonate, busulfan, nitrosoureas, carmustine, lomustine, streptozocin, platinum complex, carboplatin, alkylator, altretamine, dacarbazine, procarbazine, temozolamide, methotrexate, fludarabine, mercaptopurine, thiogaunine, cladribine, pentostatin, capecitabine, cytarabine, floxuridine, fluorouracil, gemcitabine, hydroxyurea, camptothecin, irinotecan, busufane, epothilone, azathioprine, halofuginone, sirolimus, everolimus, mytomycin, and topotecan.

Exemplary agents for targeted therapy include, but are not limited to, trastuzumab or pertuzumab (an antibody specific to tumor antigen HER-2/neu); bevacizumab (an antibody specific to vascular endothelial growth factor (VEGF)); ramucirumab (an antibody specific to VEGF receptor); nivolumab or cemiplimab (an antibody specific to programmed cell death protein 1 (PD-1)); atezolizumab, avelumab or durvalumab (an antibody specific to the ligand of programmed cell death protein 1 (PD-L1). Ipilimumab (an antibody specific to cytotoxic T-lymphocyte-associated protein 4 (CTLA-4)), rituximab (an antibody specific to CD20 on B cells), and etc.

Non-limiting examples of immunomodulatory agents for immunotherapy include, thalidomide, lenolidomide, pomalidomide, anti-PD-1 antibody, anti-PD-L1 antibody, anti-CTLA-4 antibody, interleukin (IL)-2, IL-6, IL-12, interferon-alpha (IFN-α), IFN-β, IFN-γ, granulocyte-macrophage colony-stimulating factor (GM-CSF), granulocyte colony-stimulating factor (G-CSF), and cancer vaccine (e.g., human papillomavirus (HPV) vaccine, and hepatitis B vaccine).

According to some embodiments of the present disclosure, in the case when the plasma level of arginine is equal to or greater than 60.2 μmol/L, then the pegylated rADI (ADI-PEG 20) and pembrolizumab are independently administered to the subject. In certain exemplary embodiments, the pegylated rADI (ADI-PEG 20) is administered in an amount of about 36 mg/m² body surface area weekly, and pembrolizumab is administered in the amount of about 200 mg every three weeks, so as to ameliorate or alleviate the symptoms associated with cancers. As could be appreciated, a skilled artisan or a clinical practitioner may adjust the treatment regimen (including the dosages, schedule and duration of ADI-PEG 20 and pembrolizumab treatments) in accordance with practical requirements.

Alternatively, in the case when the plasma level of arginine is less than 60.2 μmol/L, then an alternative anti-cancer treatment is administered to the subject for therapeutic purpose. As described above, the alternative anti-cancer treatment is preferably selected from the group consisting of surgery, chemotherapy, targeted therapy, radiotherapy, hormone therapy, immunotherapy, and a combination thereof. A skilled artisan or a clinical practitioner may choose a suitable treatment for the cancer patient in accordance with clinical factors of the patient.

According to some embodiments of the present disclosure, in the case when the plasma level of arginine is equal to or greater than 68.2 μmol/L, then the pegylated rADI (ADI-PEG 20), pemetrexed and cisplatin are independently administered to the subject. In certain exemplary embodiments, the pegylated rADI (ADI-PEG 20) is administered in an amount of about 36 mg/m$^2$ body surface area weekly, pemetrexed is administered in an amount of about 500 mg/m$^2$ body surface area every three weeks, and cisplatin is administered in an amount of about 75 mg/m$^2$ body surface area every three weeks, so as to ameliorate or alleviate the symptoms associated with cancers. A skilled artisan or a clinical practitioner may adjust the treatment regimen (including the dosages, schedule and duration of ADI-PEG 20, pemetrexed and cisplatin treatments) in accordance with practical requirements.

Alternatively, in the case when the plasma level of arginine is less than 68.2 μmol/L, then an alternative anti-cancer treatment is administered to the subject for therapeutic purpose. The alternative anti-cancer treatment is preferably selected from the group consisting of surgery, chemotherapy, targeted therapy, radiotherapy, hormone therapy, immunotherapy, and a combination thereof. A skilled artisan or a clinical practitioner may choose a suitable treatment for the cancer patient in accordance with clinical factors of the patient.

According to certain embodiments of the present disclosure, in the case when the plasma level of arginine is equal to or greater than 84.2 μmol/L, then the pegylated rADI (ADI-PEG 20) is administered to the subject alone, without combining with any additional treatments. In certain exemplary embodiments, the pegylated rADI (ADI-PEG 20) is administered in an amount of about 18 mg/m$^2$ body surface area weekly, so as to ameliorate or alleviate the symptoms associated with cancers. A skilled artisan or a clinical practitioner may adjust the treatment regimen (including the dosage, schedule and duration of ADI-PEG 20 treatment) in accordance with practical requirements.

By contrast, in the case when the plasma level of arginine is less than 84.2 μmol/L, then an alternative anti-cancer treatment is administered to the subject for therapeutic purpose. The alternative anti-cancer treatment is preferably selected from the group consisting of surgery, chemotherapy, targeted therapy, radiotherapy, hormone therapy, immunotherapy, and a combination thereof. A skilled artisan or a clinical practitioner may choose a suitable treatment for the cancer patient in accordance with clinical factors of the patient.

According to certain embodiments of the present disclosure, in the case when the plasma level of arginine is equal to or greater than 97.5 μmol/L, then the pegylated rADI (ADI-PEG 20) and docetaxel are independently administered to the subject. In some exemplary embodiments, the pegylated rADI (ADI-PEG 20) is administered in an amount of about 36 mg/m$^2$ body surface area weekly, and docetaxel is administered in an amount of about 75 mg/m$^2$ body surface area every three weeks, so as to ameliorate or alleviate the symptoms associated with cancers. A skilled artisan or a clinical practitioner may adjust the treatment regimen (including the dosages, schedule and duration of ADI-PEG 20 and docetaxel treatments) in accordance with practical requirements.

Alternatively, in the case when the plasma level of arginine is less than 97.5 μmol/L, then an alternative anti-cancer treatment is administered to the subject for therapeutic purpose. The alternative anti-cancer treatment is preferably selected from the group consisting of surgery, chemotherapy, targeted therapy, radiotherapy, hormone therapy, immunotherapy, and a combination thereof. A skilled artisan or a clinical practitioner may choose a suitable treatment for the cancer patient in accordance with clinical factors of the patient.

According to certain embodiments of the present disclosure, in the case when the plasma level of arginine is equal to or greater than 122 μmol/L, then the pegylated rADI (ADI-PEG 20) and cisplatin are independently administered to the subject. In some exemplary embodiments, the pegylated rADI (ADI-PEG 20) is administered in an amount of about 36 mg/m$^2$ body surface area weekly, and cisplatin is administered in an amount of about 30 mg/m$^2$ body surface area weekly for three weeks (week 1 to week 3) followed by one week (week 4) of rest period in one treatment cycle, so as to ameliorate or alleviate the symptoms associated with cancers. A skilled artisan or a clinical practitioner may adjust the treatment regimen (including the dosages, schedule and duration of ADI-PEG 20 and cisplatin treatments) in accordance with practical requirements.

By contrast, in the case when the plasma level of arginine is less than 122 μmol/L, then an alternative anti-cancer treatment is administered to the subject for therapeutic purpose. The alternative anti-cancer treatment is preferably selected from the group consisting of surgery, chemotherapy, targeted therapy, radiotherapy, hormone therapy, immunotherapy, and a combination thereof. A skilled artisan or a clinical practitioner may choose a suitable treatment for the cancer patient in accordance with clinical factors of the patient.

The cancers treatable with the present method include, but are not limited to, breast cancer, brain tumor, colorectal cancer, head and neck squamous cell carcinoma, HCC, leukemia, AML, lymphoma, lung cancer, melanoma, mesothelioma, MPM, neuroblastoma, ovarian cancer, pancreatic cancer, prostate cancer, renal cell carcinoma, and sarcoma. According to some exemplary embodiments, the cancer is HCC. In one specific example, the cancer is advanced HCC.

The subject is a mammal, such as a human, a mouse, a rat, a guinea pig, a monkey, a sheep, a goat, a cat, a dog, a horse, or a chimpanzee. Preferably, the subject is a human.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods

Patient Enrollment

The plasma samples from patients receiving arginine deprivation therapy were used in this study. Patients (including cohort-1 to cohort-6) enrolled in the study were diagnosed with advanced stage of HCC and had joined the clinical trial of ADI-PEG 20 in Taiwan. The de-linked samples and clinicopathological parameters were used for post hoc analysis.

The cohort-1, containing 422 patients, received ADI-PEG 20 monotherapy, in which ADI-PEG 20 was intramuscularly administered to each patient at a dose of 18 mg/m² weekly, until disease progression or unacceptable adverse event occurred or other withdrawal criteria met.

The cohort-2, containing 31 patients, received ADI-PEG 20 in combination with docetaxel, in which ADI-PEG 20 was intramuscularly administered to each patient at a dose of 36 mg/m² weekly, and docetaxel was intravenously administered at a dose of 75 mg/m² every three week, until disease progression or unacceptable adverse event occurred or other withdrawal criteria met.

The cohort-3, containing 78 patients, received ADI-PEG 20 in combination with cisplatin, in which ADI-PEG 20 was intramuscularly administered to each patient at a dose of 36 mg/m² weekly, and cisplatin was intravenously administered to each patient at a dose of 30 mg/m² weekly for three weeks (week 1 to week 3) followed by one week (week 4) of rest period in one treatment cycle, until disease progression or unacceptable adverse event occurred or other withdrawal criteria met.

The cohort-4, containing 39 patients, received ADI-PEG 20 in combination with modified FOLFOX6 regimen (mFOLFOX6 regimen, composed of 85 mg/m² oxaliplatin, 400 mg/m² bolus of 5-FU, and 400 mg/m² leucovorin on the first day, followed by 2,400 mg/m² of 5-FU as a continuous infusion in 2 days), in which ADI-PEG 20 was intramuscularly administered to each patient at a dose of 36 mg/m² weekly, and mFOLFOX6 regimen was intravenously administered to each patient every two weeks, until disease progression or unacceptable adverse event occurred or other withdrawal criteria met.

The cohort-5, containing 111 patients, received ADI-PEG 20 in combination with pemetrexed and cisplatin, in which ADI-PEG 20 was intramuscularly administered to each patient at a dose of 36 mg/m² weekly, pemetrexed was intravenously administered to each patient at a dose of 500 mg/m² every three weeks, and cisplatin was intravenously administered to each patient at a dose of 75 mg/m² every three weeks, until disease progression or unacceptable adverse event occurred or other withdrawal criteria met.

The cohort-6, containing 27 patients, received ADI-PEG 20 in combination with pembrolizumab, in which ADI-PEG 20 was intramuscularly administered to each patient at a dose of 36 mg/m² weekly, and pembrolizumab was intravenously administered to each patient at a dose of 200 mg every three weeks, until disease progression or unacceptable adverse event occurred or other withdrawal criteria met.

Therapeutic Outcomes Evaluation

The duration of overall survival (OS) of patients in cohort-1 and cohort-5 was calculated from the date of patients included for randomization to the date of death, regardless of any causes, or the date of losing follow-up. The duration of OS of patients in cohort-2, cohort-3, cohort-4 and cohort-6 was calculated as the time from the first dose of study treatment until death from any case; in the case when a subject is alive or lost to follow up, they were censored at last date of contact.

Statistical Analysis

The optimal cut-off point of plasma arginine level for survival outcomes was determined using maximally selected log-rank statistics. Kaplan-Meier method was employed to estimate the median OS of patients. A p value <0.05 determined by log-rank test was considered statistically significant. Statistical analysis was conducted using software.

Example 1 Correlation of Plasma Arginine Level with OS in Advanced HCC Patients Receiving Arginine Deprivation Therapy Alone or in Combination with Additional Treatment To investigate whether the plasma level of arginine was correlated with OS in cancer patients, maximally selected log-rank statistics was performed. The analytic results were respectively depicted in FIGS. 1-12 and summarized in Table 1-3.

TABLE 1

| | | | | | | | | |
|---|---|---|---|---|---|---|---|---|
| Correlation of plasma arginine level with OS of cancer patients receiving specified treatments | | | | | | | | |
| Cohort | Treatment | Indication | Sample Size | cut-off[1] | Arginine (umo/L) | # of Event | # of Censored | Median OS[2] (95% CI)[3] | P-value[4] |
| cohort-1 | ADI-PEG 20 (18 mg/m²) | HCC | 184 | 84.2 | >=84.2 | 143 | 41 | 8.6 (7.3, 10.5) | 0.0057 |
| | | | 238 | | <=84.2 | 202 | 36 | 5.7 (4.9. 7.2) | |
| cohort-5 | ADI-PEG 20 (36 mg/m²) + Pemetrexed (500 mg/m²) + Cisplatin (75 mg/m²) | Malignant Pleural Mesothelioma (MPM) | 72 | 68.2 | >=68.2 | 58 | 14 | 12.5 (9.8, 14.2) | 0.0011 |
| | | | 39 | | <68.2 | 36 | 3 | 6.5 (3.8, 8.8) | |

[1]Maximally Selected log-rank, statistics.
[2]Months.
[3]Kaplan-Meier product-limit estimates.
[4]p-value comparing the treatment groups is based on the log-rank test.

TABLE 2

| | | | | | | | | |
|---|---|---|---|---|---|---|---|---|
| Correlation of plasma arginine level with OS of cancer patients receiving specified treatments | | | | | | | | |
| Protocol No. | Treatment | Indication | Sample Size | cut-off[1] | Arginine (umo/L) | # of Event | # of Censored | Median OS[2] (95% CI)[3] | P-value[4] |
| cohort-2 | ADI-PEG 20 (36 mg/m²) + Docetaxel(75 mg/m²) | Advanced Solid Tumors with Emphasis on Castration Resistant Prostate Cancer (CRPC) and Advanced Non-Small Cell Lung Cancer (NSCLC) | 12 | 97.5 | >=97.5 | 5 | 7 | 40.7 (7.2, 40,7) | 0.0117 |
| | | | 19 | | <97.5 | 14 | 5 | 14.6 (5.7, 16.0) | |

TABLE 2-continued

Correlation of plasma arginine level with OS of cancer patients receiving specified treatments

| Protocol No. | Treatment | Indication | Sample Size | cut-off[1] | Arginine (umo/L) | # of Event | # of Censored | Median OS[2] (95% CI)[3] | P-value[4] |
|---|---|---|---|---|---|---|---|---|---|
| cohort-3 | ADI-PEG 20 (36 mg/m2) + Cisplatin (30 mg/m$^2$) | HCC with coexistent biliary tract carcinoma (BTC) of BTC Only | 23 | 122 | >=122 | 16 | 7 | 15.7 (8.9. 28.5) | 0.0006 |
| | | Cutaneous Melanoma Ovarian Carcinoma Uveal Melanoma | 55 | | <122 | 47 | | 6.4 (3.4. 8.2) | |
| cohort-4 | ADI-PEG 20 (36 mg/m$^2$) + FOLFOX | Gastro-esophageal Cancer Colorectal Cancer | 37 | 34 | >=34 | 30 | 7 | 9.5 ( 7.5, 15.1) | 0.0083 |
| | | Hepatocellular Carcinoma | 2 | | <34 | 2 | 0 | 4.3 (4.0. 4.6) | |
| cohort-6 | ADI-PEG 20 36 mg/m$^2$ + Pembrolizumab 200 mg | Advanced Solid Cancers | 10 | 60.2 | >=60.2 | 2 | 8 | (2.5,) | 0.0119 |
| | | | 17 | | <60.2 | 13 | 4 | 6.6 (1.8. 7.8) | |

[1]Maximally Selected log-rank statistics.
[2]Months.
[3]Kaplan-Meier product-limit estimates.
[4]P-value comparing the treatment groups is based on the log-rank test.

Example 2. The Procedure of Determining the Arginine Cut-Off Point (e.g. HCC)

First step—to determine the cut-off value of arginine. HCC patients agree to join the Polaris HCC clinical study, and Polaris collect patients' plasma before first treatment of ADI-PEG 20. Then, pharmacodynamics will be assessed by measurement of peripheral blood levels of arginine and citrulline by LCMS. Total of 633 patients (422 for ADI-PEG 20 group and 211 for placebo group) were enrolled in the study. Then, clinical database is locked once the number of deaths reach the requirement of sample size calculation at the beginning of study design. Further, the statistician calculates each patient's overall survival. The Arginine cut-off point is determined using the Maximally Selected log-rank statistics (statistician inputs each patient's arginine value and OS into the statistical model).

Second step—to validate the efficiency of arginine cut-off point. 422 HCC patient who were treated as ADI-PEG 20 are categorized into two groups: high arginine group and low arginine group. Then, the overall survival is summarized using the Kaplan-Meier product-limit estimates. Point estimates (25th, 50th, and 75th percentiles) along with 95% confidence intervals will be provided by treatment group. Survival estimates will also be shown graphically for each treatment group. Further, treatments will be compared using a stratified log-rank test.

In one embodiment, a method of in vitro identifying the arginine threshold in biological samples of cancer subjects to predict whether the subjects respond to arginine deprivation therapy, comprising: providing a biological sample, the biological sample taken from a subject prior to be administrated an arginine deprivation agent; determining an arginine concentration, measuring the arginine concentration in the biological sample; calculating an overall survival, the overall survival statistics are assessed after the subjects undergo the arginine deprivation therapy: the arginine cut-off point is determined through the following steps: (1) Identifying the highest value of the standardized log-rank statistics on the Y-axis of the statistical chart; (2) Determining the highest point on the Y-axis and find the corresponding arginine value on the X-axis; and (3) The level of arginine corresponding to this highest point is considered the arginine cut-off value. (for example, arginine cut-off point is 84.2 μmol/L in cohort-1, and please refer to FIG. 1); calculating an arginine threshold, based on the arginine cut-off point to be the highest arginine value and gradually decrease the value of arginine and calculate the corresponding p-value for each arginine value, continuing this process until the p-value for the nth arginine value is higher than 0.05, then the arginine value corresponding to the (n−1)th arginine value is the arginine threshold (please refer Table 3); wherein, when the arginine concentration of the subjects is greater than or equal to the arginine threshold, it means that the cancer subject well responds to the arginine deprivation therapy.

Figure 2:
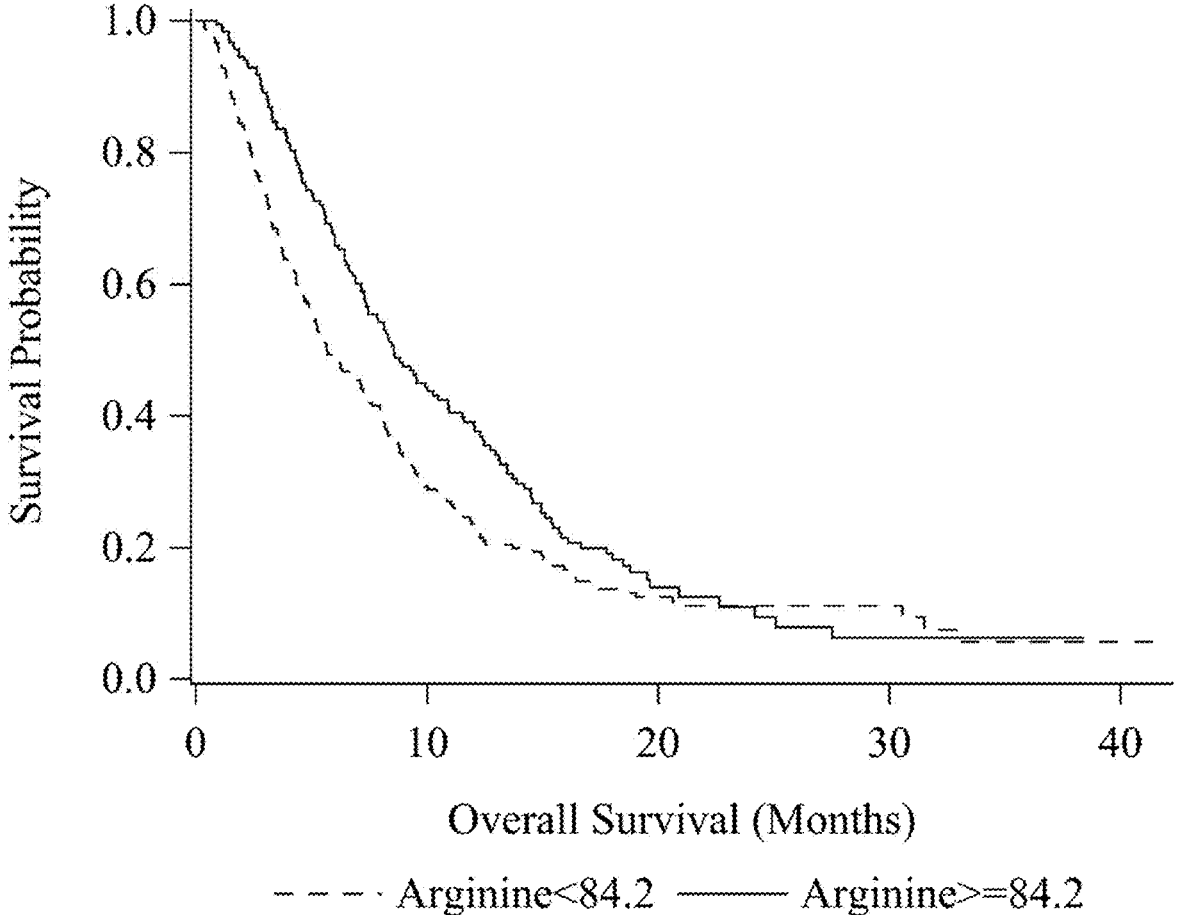
FIG. 2 is a line chart depicting the correlation of plasma arginine level with OS in cancer patients receiving ADI-PEG 20 alone according to Example 1 of the present disclosure

According to the results, 422 patients in cohort-1 were treated with ADI-PEG 20 18 mg/m$^2$, with the estimated arginine cut-off point for overall survival set at 84.2 μmol/L. The maximum log-rank statistic recorded was M=2.8792 (FIG. 1). The difference in overall survival time between the two groups, defined by a arginine cut-off point of 84.2 μmo/L, is illustrated in the figure. The high arginine group (arginine >=84.2 μmol/L) had a median OS of 8.6 months (95% CI: 7.3, 10.5), while the low arginine group (arginine <84.2 μmol/L) has a medina OS of 5.7 month (95% CI: 4.9, 7.2), indicating that the high arginine group experienced longer survival (p-value=0.0057) in cohort-1 (FIG. 2 and Table 1).

According to prior ADI-PEG 20 monotherapy Phase HCC study, the cut-off value of arginine was 84.2 μmol/L based on the maximally selected rank statistics. Patients with arginine levels ≥84.2 μmol/L may survive longer than those with arginine levels <84.2 μmol/L.

To enroll more patients, the prognostic variable analysis was used to determine the arginine threshold. Based on the arginine cut-off point of 84.2 μmol/L, the highest arginine value is considered, followed by a gradual decrease in arginine values as follows: 83 μmol/L, 82 μmol/L, 81 μmol/L, 80 μmol/L, and 79 μmol/L. In Table 3, the significant corresponding *P-value of each arginine is less than 0.05. However, when the arginine is 78 μmol/L, and for the first time, the *P-value is higher than 0.05. Therefore, the 78 μmol/L is defined as the nth arginine. The previous one (n−1)th arginine, which is 79 μmol/L, serves as the arginine threshold. The survival of higher then the arginine threshold is longer than low arginine, reaching statistical significance. According to the statistical result mostly the arginine threshold is less than the arginine cut-off point among 5%~10% (Table 3).

TABLE 3

| Cut-off point of Arginine (µmol/L) | Level | N | # of event | # of censor | Median OS (95% CI) | P-value | Judgment of nth arginine value |
|---|---|---|---|---|---|---|---|
| | | | | | The cut-off value of cohort-1 | | |
| 78 | >=78 | 215 | 172 | 43 | 8.17 (6.9, 9.4) | 0.0671 | nth |
| | <78 | 207 | 173 | 34 | 6.17 (4.93, 7.63) | | |
| 79 | >=79 | 211 | 168 | 43 | 8.17 (6.9, 9.53) | 0.0414* | (n-1)th |
| | <79 | 211 | 177 | 34 | 5.9 (4.9, 7.43) | | |
| 80 | >=80 | 208 | 165 | 43 | 8.3 (7.13, 9.57) | 0.0223* | |
| | <80 | 214 | 180 | 34 | 5.7 (4.9, 7.4) | | |
| 81 | >=81 | 203 | 161 | 42 | 8.3 (7.13, 9.93) | 0.0383* | |
| | <81 | 219 | 184 | 35 | 5.7 (4.9, 7.4) | | |
| 82 | >=82 | 199 | 158 | 41 | 8.3 (7.13, 9.93) | 0.0342* | |
| | <82 | 223 | 187 | 36 | 5.7 (4.93, 7.4) | | |
| 83 | >=83 | 196 | 155 | 41 | 8.47 (7.3, 10.0) | 0.0211* | |
| | <83 | 226 | 190 | 36 | 5.7 (4.93, 7.33) | | |
| 84.2 | >=84.2 | 184 | 143 | 41 | 8.57 (7.33, 10.47) | 0.0057* | arginine cut-off point |
| | <84.2 | 238 | 202 | 36 | 5.7 (4.9, 7.3) | | |

*P-value of less than 0.05 is considered significant.

Figure 3:
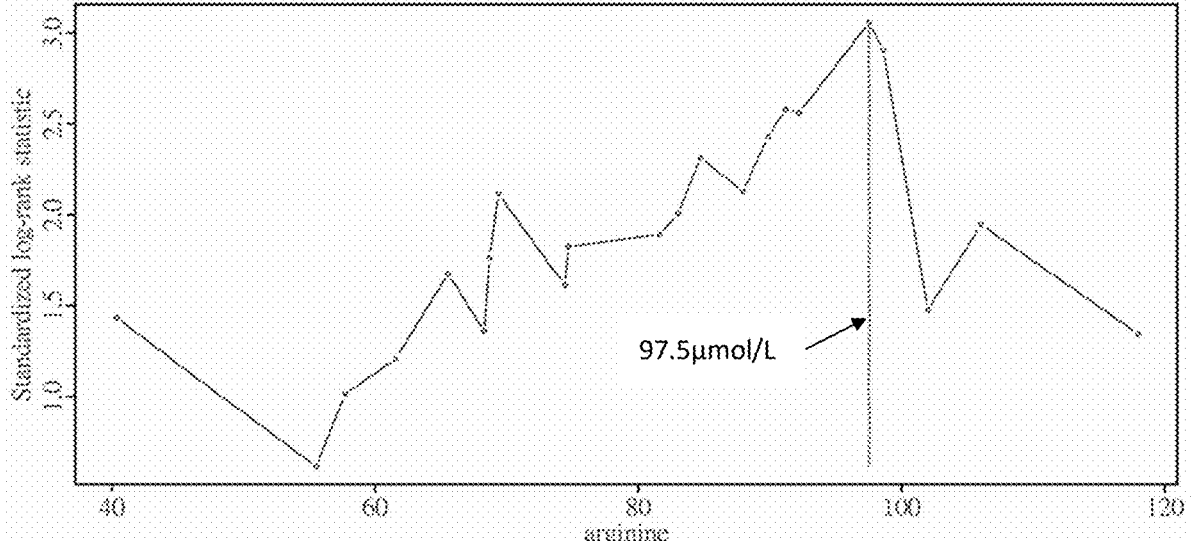
FIG. 3 shows the chart illustrating the treatment of cancer patients with ADI-PEG 20+Docetaxel, analyzed via using the maximum log-rank statistic to finding the arginine cut-off.
Figure 4:
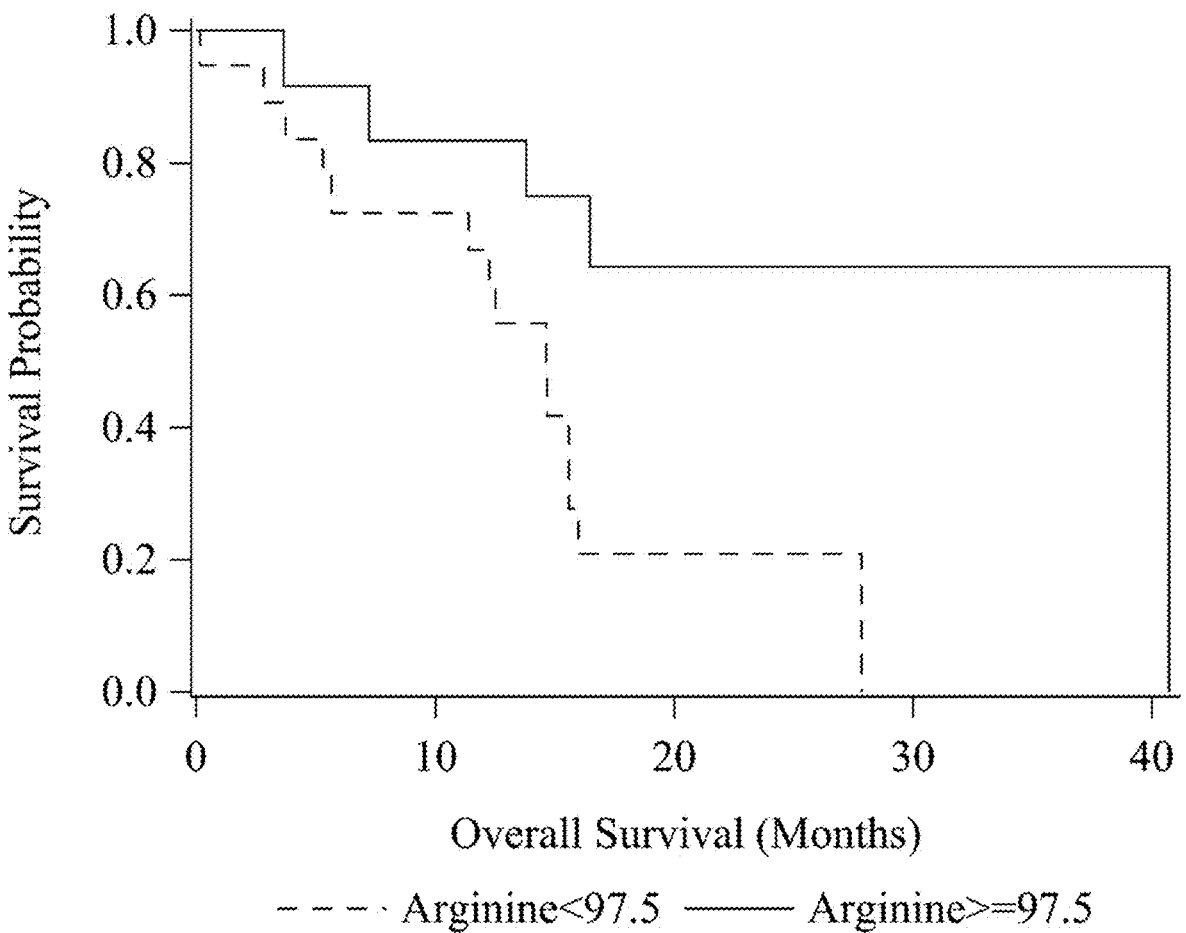
FIG. 4 is a line chart depicting the correlation of plasma arginine level with OS in cancer patients receiving ADI-PEG 20 in combination with docetaxel according to Example 1 of the present disclosure.

According to the results, 31 patients in cohort-2 were treated with ADI-PEG 20 36 mg/m$^2$+Docetaxel 75 mg/m$^2$, with the estimated arginine cut-off point for overall survival set at 97.5 µmol/L. The maximum log-rank statistic recorded was M=3.0599 (FIG. 3). The difference in overall survival time between the two groups, defined by a arginine cut-off point of 97.5 µmo/L, is illustrated in the figure. The high arginine group (arginine >=97.5 µmo/L) had a median OS of 40.7 months (95% CI: 7.2, 40.7), while the low arginine group (arginine <97.5 µmol/L) has a medina OS of 14.6 month (95% CI: 5.7, 16.0), indicating that the high arginine group experienced longer survival (p-value=0.0117) in cohort-2 (FIG. 4 and Table 2).

Figure 5:
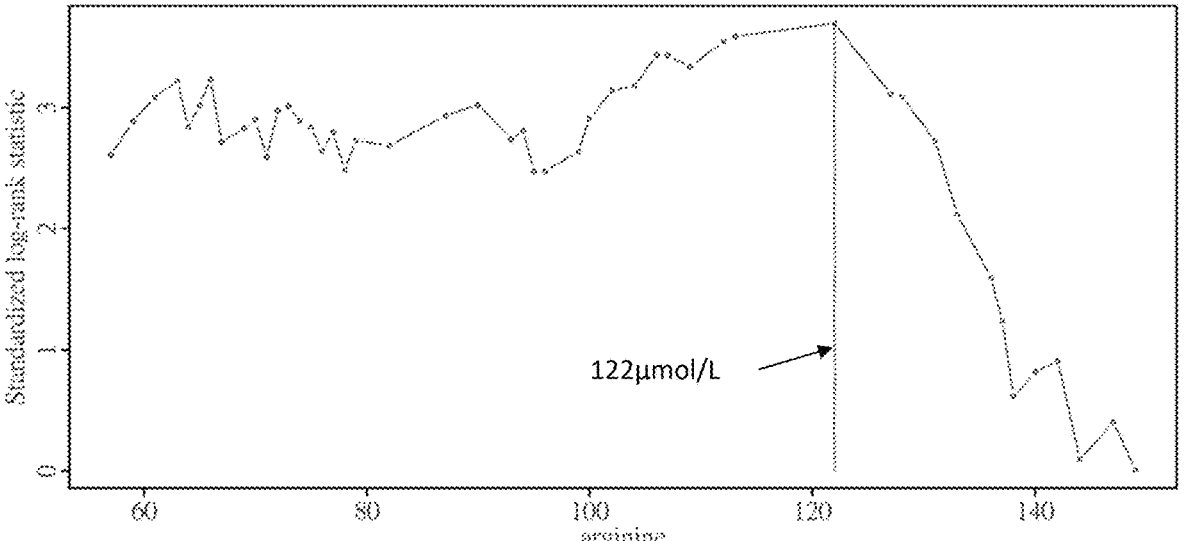
FIG. 5 shows the chart illustrating the treatment of cancer patients with ADI-PEG 20+Cisplatin, analyzed via using the maximum log-rank statistic to finding the arginine cut-off.
Figure 6:
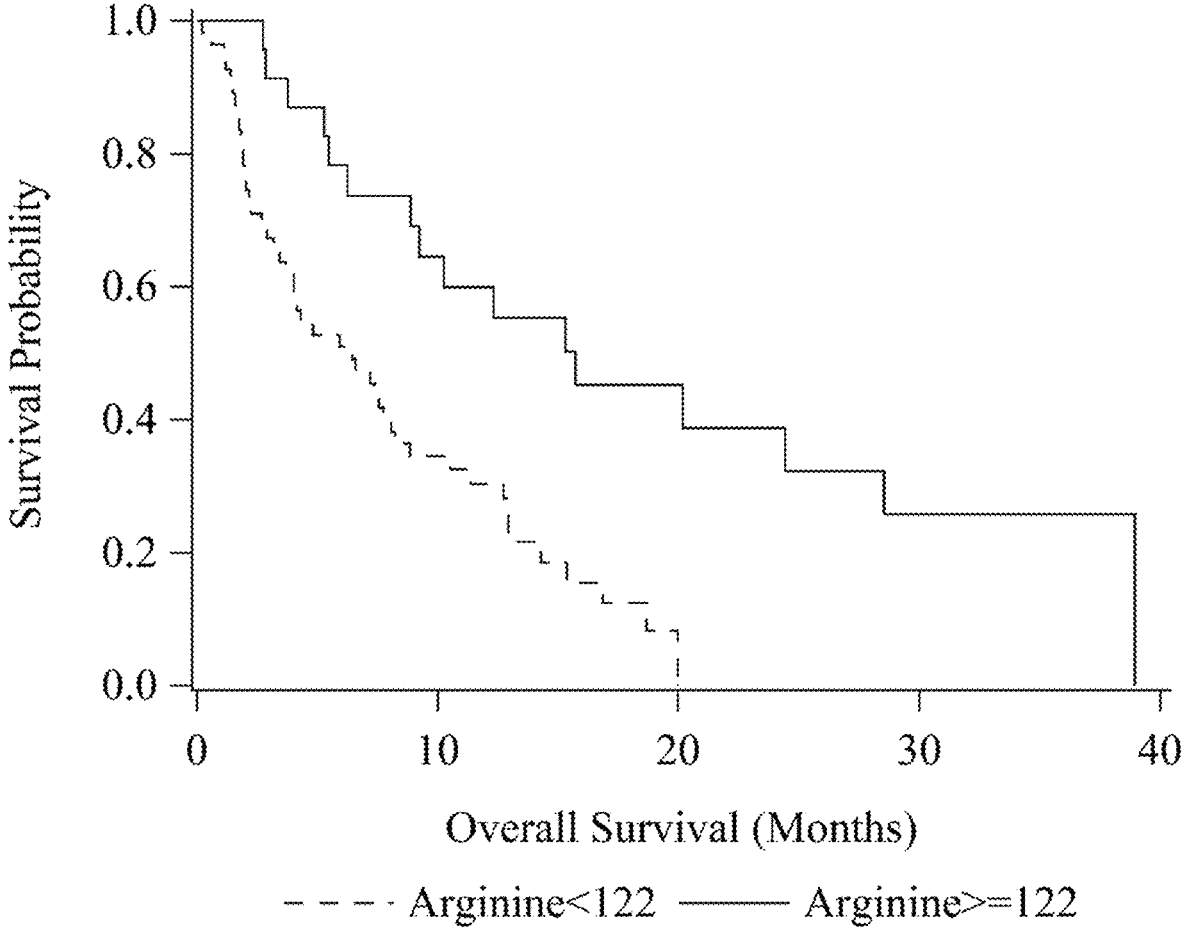
FIG. 6 is a line chart depicting the correlation of plasma arginine level with OS in cancer patients receiving ADI-PEG 20 in combination with cisplatin according to Example 1 of the present disclosure.

According to the results, 78 patients in cohort-3 were treated with ADI-PEG 20 36 mg/m$^2$+Cisplatin 30 mg/m$^2$, with the estimated arginine cut-off point for overall survival set at 122 µmo/L. The maximum log-rank statistic recorded was M=3.6943 (FIG. 5). The difference in overall survival time between the two groups, defined by a arginine cut-off point of 122 µmol/L, is illustrated in the figure. The high arginine group (arginine >=122 µmol/L) had a median OS of 15.7 months (95% CI: 8.9, 28.5), while the low arginine group (arginine <122 µmol/L) has a medina OS of 6.4 month (95% CI: 3.4, 8.2), indicating that the high arginine group experienced longer survival (p-value=0.0006) in cohort-3 (FIG. 6 and Table 2).

Figure 7:
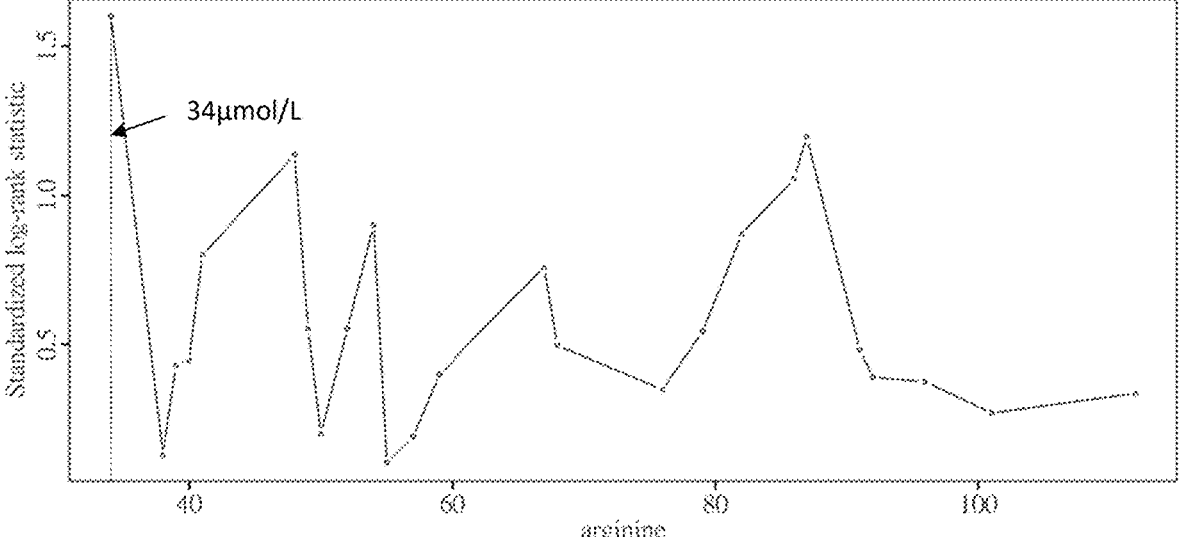
FIG. 7 shows the chart illustrating the treatment of cancer patients with ADI-PEG 20+FOFLOX, analyzed via using the maximum log-rank statistic to finding the arginine cut-off.
Figure 8:
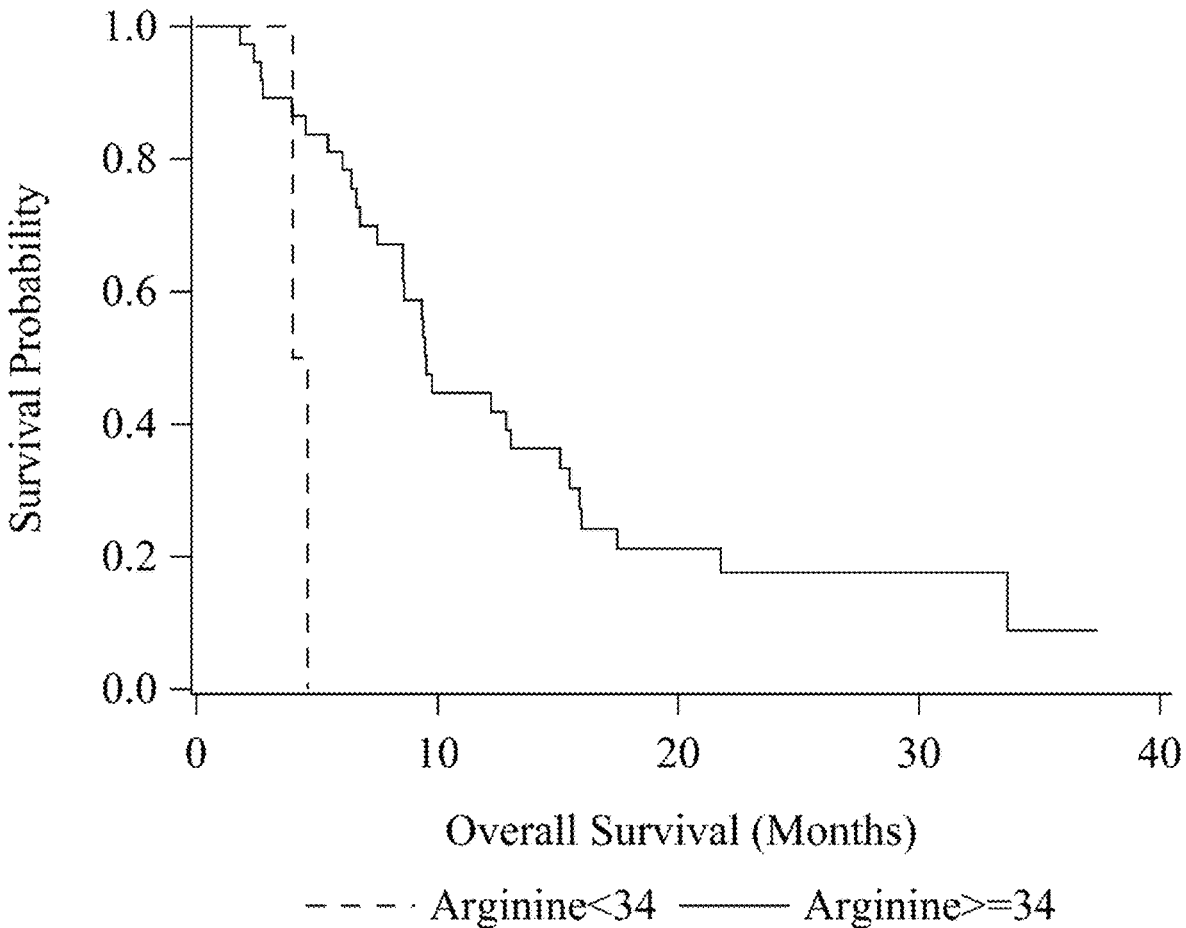
FIG. 8 is a line chart depicting the correlation of plasma arginine level with OS in cancer patients receiving ADI-PEG 20 in combination with mFOLFOX6 according to Example 1 of the present disclosure.

According to the results, 39 patients in cohort-4 were treated with ADI-PEG 20 36 mg/m$^2$+FOFLOX, with the estimated arginine cut-off point for overall survival set at 34 µmo/L. The maximum log-rank statistic recorded was M=1.6007 (FIG. 7). The difference in overall survival time between the two groups, defined by a arginine cut-off point of 34 µmol/L, is illustrated in the figure. The high arginine group (arginine >=34 µmol/L) had a median OS of 9.5 months (95% CI: 7.5, 15.1), while the low arginine group (arginine <34 µmol/L) has a medina OS of 4.3 month (95% CI: 4.0, 4.6), indicating that the high arginine group experienced longer survival (p-value=0.00083) in cohort-4 (FIG. 8 and Table 2).

Figure 9:
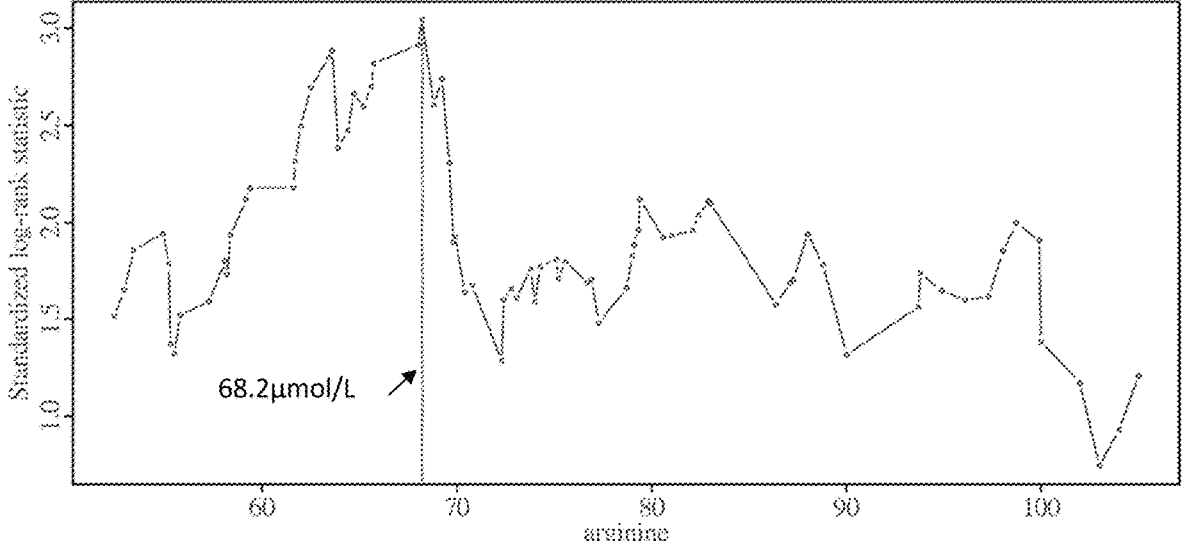
FIG. 9 shows the chart illustrating the treatment of cancer patients with ADI-PEG 20+Pemetrexed+Cisplatin, analyzed via using the maximum log-rank statistic to finding the arginine cut-off.
Figure 10:
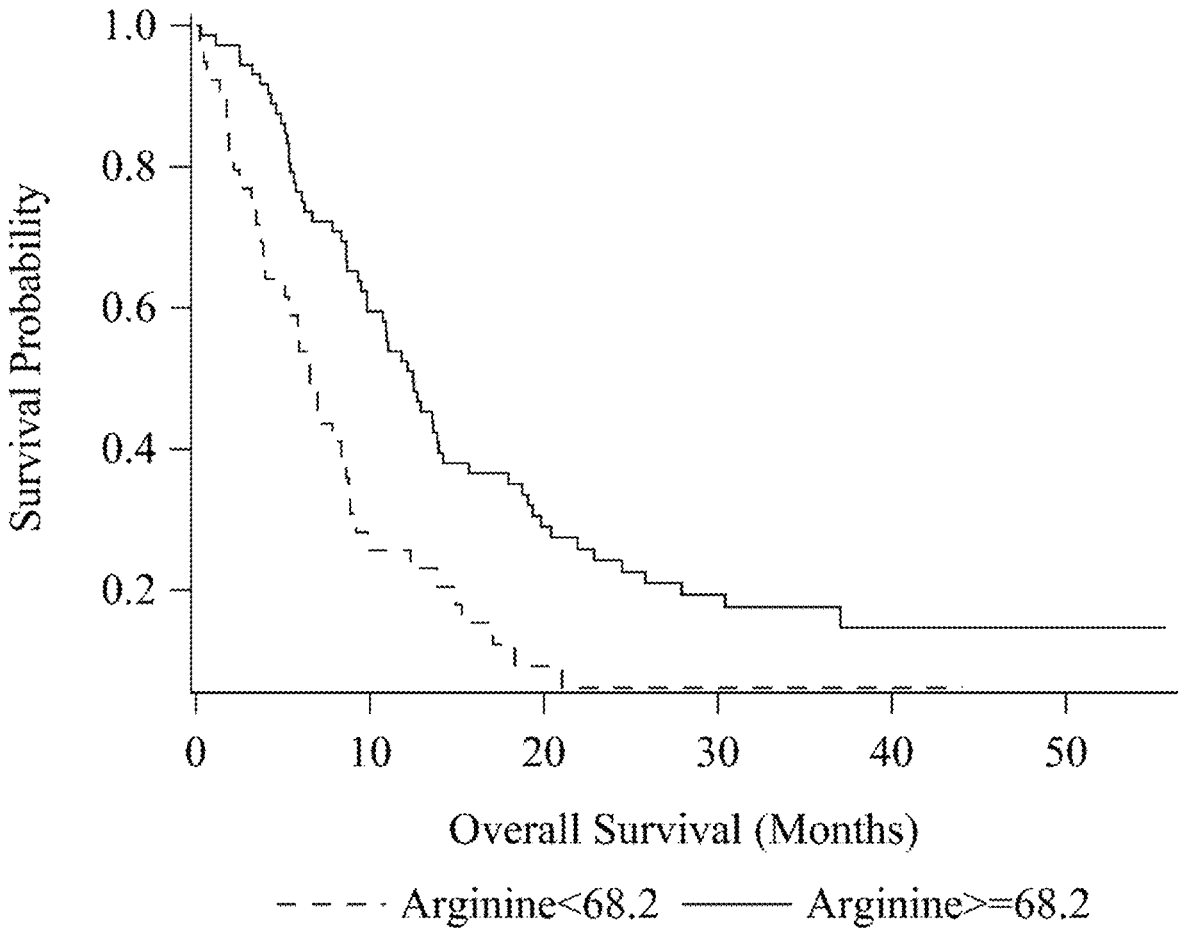
FIG. 10 is a line chart depicting the correlation of plasma arginine level with OS in cancer patients receiving ADI-PEG 20 in combination with pemetrexed and cisplatin according to Example 1 of the present disclosure.

According to the results, 111 patients in cohort-5 were treated with ADI-PEG 20 36 mg/m$^2$+Pemetrexed 500 mg/m$^2$+Cisplatin 75 mg/m$^2$, with the estimated arginine cut-off point for overall survival set at 68.2 µmol/L. The maximum log-rank statistic recorded was M=3.043 (FIG. 9). The difference in overall survival time between the two groups, defined by a arginine cut-off point of 68.2 µmol/L, is illustrated in the figure below. The high arginine group (arginine >=68.2 µmol/L) had a median OS of 12.5 months (95% CI: 9.8, 14.2), while the low arginine group (arginine <68.2 µmol/L) has a medina OS of 6.5 month (95% CI: 3.8, 8.8), indicating that the high arginine group experienced longer survival (p-value=0.0011) in cohort-5 (FIG. 10 and Table 1).

Figure 11:
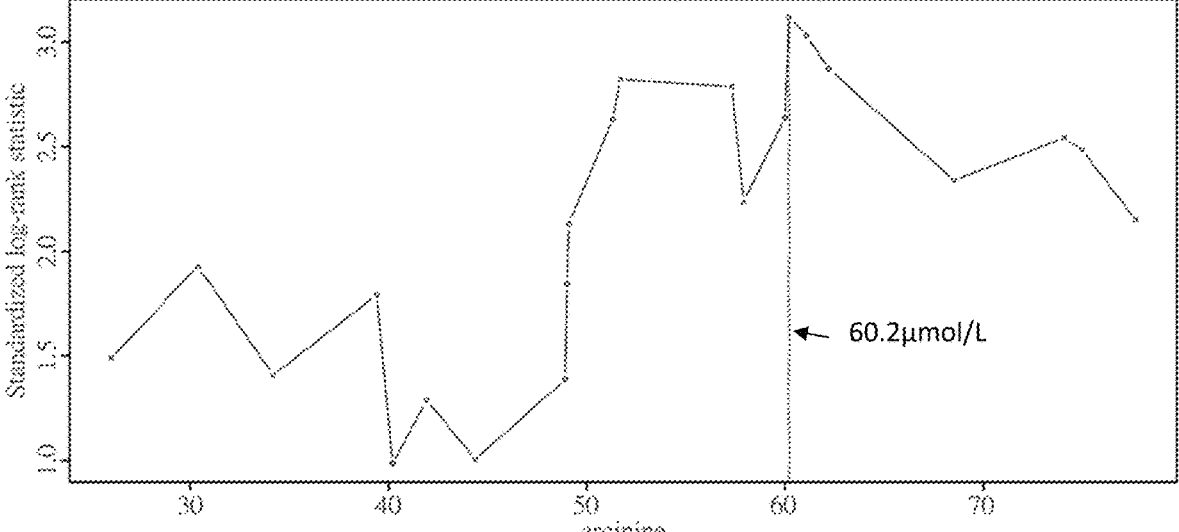
FIG. 11 shows the chart illustrating the treatment of cancer patients with ADI-PEG 20+Pembrolizumab, analyzed via using the maximum log-rank statistic to finding the arginine cut-off.
Figure 12:
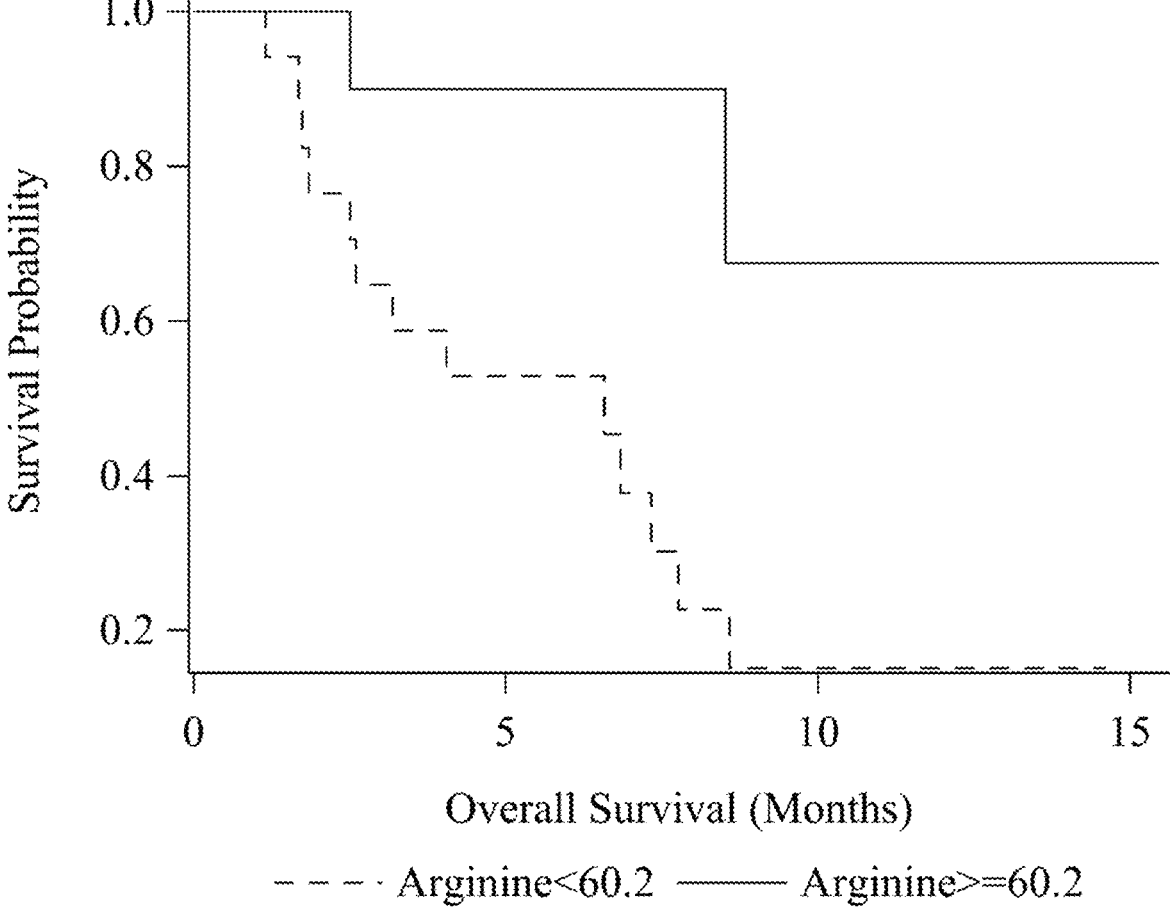
FIG. 12 is a line chart depicting the correlation of plasma arginine level with OS in cancer patients receiving ADI-PEG 20 in combination with pembrolizumab according to Example 1 of the present disclosure.

According to the results, 27 patients were treated with ADI-PEG 20 36 mg/m$^2$+Pembrolizumab 200 mg, with the estimated arginine cut-off point for overall survival set at 60.2 µmol/L. The maximum log-rank statistic recorded was M=3.0899 (FIG. 11). The difference in overall survival time between the two groups, defined by a arginine cut-off point of 60.2 µmol/L, is illustrated in the figure below. The median OS cannot be estimated due to high censoring rate, as most subjects are still alive. The low arginine group (arginine <60.2 µmol/L) has a medina OS of 6.6 month (95% CI: 1.8, 7.8), indicating that the high arginine group experienced longer survival (p-value=0.0119) in cohort-6 (FIG. 12 and Table 2).

Taken together, the plasma level of arginine could predict the outcome (i.e., OS) of arginine deprivation therapy alone or in combination with different anti-cancer treatments, including FOLFOX, docetaxel, cisplatin, pemetrexed and pembrolizumab.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method of in vitro identifying the arginine threshold in biological samples of cancer subjects to predict whether the subjects respond to arginine deprivation therapy, comprising:

providing a biological sample, the biological sample taken from a subject prior to be administrated an arginine deprivation agent;

determining an arginine concentration, measuring the arginine concentration in the biological sample;

calculating an overall survival, the overall survival statistics are assessed after the subjects undergo the arginine deprivation therapy;

calculating an arginine cut-off point, inputting the arginine concentration and the overall survival of the subjects into the statistical method of maximally selected log-rank statistics to determine the arginine cut-off point; and calculating an arginine threshold, based on the arginine cut-off point to be the highest arginine value and gradually decrease the value of arginine and calculate the corresponding p-value for each arginine value, continuing this process until the p-value for the nth arginine value is higher than 0.05, then the $(n-1)$th arginine value is the arginine threshold, wherein, when the arginine concentration of the subjects is greater than or equal to the arginine threshold, it means that the cancer subject responds well to the arginine deprivation therapy.

2. The method according to claim 1, wherein the results of the maximally selected log-rank statistics further comprising a statistical chart generated with levels of arginine plotted on the X-axis and the standardized log-rank statistics on the Y-axis.

3. The method according to claim 2, wherein the arginine cut-off point is determined through the following steps:

identifying the highest value of the standardized log-rank statistics on the Y-axis of the statistical chart; and determining the highest point on the Y-axis and find the corresponding arginine value on the X-axis, wherein the level of arginine corresponding to this highest point is considered the arginine cut-off value.

4. The method according to claim 1, wherein the arginine threshold is analysis by the statistics of the log-rank test.

5. The method according to claim 1, wherein the arginine threshold is less than the arginine cut-off point among 5%~10%.

6. The method according to claim 1, wherein the cancer is selected from the group consisting of breast cancer, brain tumor, colorectal cancer, head and neck squamous cell carcinoma, hepatocellular carcinoma (HCC), leukemia, acute myeloid leukemia (AML), lymphoma, lung cancer, melanoma, mesothelioma, malignant pleural mesothelioma (MPM), neuroblastoma, ovarian cancer, pancreatic cancer, prostate cancer, renal cell carcinoma, sarcoma, and a combination thereof.

7. The method according to claim 6, wherein the cancer is the hepatocellular carcinoma (HCC) and the arginine cut-off point is 84.2 μmol/L.

8. The method according to claim 6, wherein the cancer is the hepatocellular carcinoma (HCC) and the arginine threshold is 79 μmol/L.

9. The method according to claim 1, wherein the biological sample is plasma.

10. The method according to claim 1, wherein the arginine deprivation agent is selected from the group consisting of a recombinant arginine deiminase (rADI), a recombinant arginase (rArg), a recombinant arginine decarboxylase (rADC), a pegylated form of the rADI, the rArg, the rADC, difluoromethylornithine (DFMO) and a combination thereof.

11. The method according to claim 1, wherein the arginine deprivation agent is in further combination with an anti-cancer agent.

12. The method according to claim 11, wherein the anti-cancer agent is selected from the group consisting of FOLFOX, docetaxel, cisplatin, pemetrexed, pembrolizumab, and a combination thereof.

13. The method according to claim 12, wherein the arginine deprivation agent is pegylated form of the recombinant arginine deiminase (rADI) and the anti-cancer agent is cisplatin and the arginine cut-off point value is 122 μmol/L.

* * * * *